(12) United States Patent
Rowe

(10) Patent No.: US 12,066,414 B2
(45) Date of Patent: Aug. 20, 2024

(54) MODULAR GAS DETECTION SYSTEM FOR A WELLBORE

(71) Applicant: Halliburton Energy Services, Inc., Houston, TX (US)

(72) Inventor: Mathew Dennis Rowe, Spring, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 273 days.

(21) Appl. No.: 17/748,741

(22) Filed: May 19, 2022

(65) Prior Publication Data

US 2023/0408466 A1 Dec. 21, 2023

(51) Int. Cl.

| | |
|---|---|
| *G01N 30/78* | (2006.01) |
| *G01N 30/30* | (2006.01) |
| *G01N 30/32* | (2006.01) |
| *G01N 30/86* | (2006.01) |
| *G01N 33/24* | (2006.01) |
| *G01N 30/00* | (2006.01) |

(Continued)

(52) U.S. Cl.
CPC .............. *G01N 30/78* (2013.01); *G01N 30/30* (2013.01); *G01N 30/32* (2013.01); *G01N 30/8665* (2013.01); *G01N 33/241* (2013.01); *G01N 2030/0095* (2013.01); *G01N 2030/3007* (2013.01); *G01N 2030/3053* (2013.01); *G01N 2030/685* (2013.01); *G01N 2030/8854* (2013.01)

(58) Field of Classification Search
CPC ........ G01N 30/78; G01N 30/30; G01N 30/32; G01N 30/8665; G01N 33/241; G01N 2030/0095; G01N 2030/3007; G01N 2030/3053; G01N 2030/685; G01N 2030/8854; G01N 33/0047; G01N 30/00; E21B 49/08; E21B 49/0875
See application file for complete search history.

(56) References Cited

U.S. PATENT DOCUMENTS 7,598,487 B2 * 10/2009 Qian ................. G01N 30/7206
  73/23.35
8,615,364 B1    12/2013 Selman et al.
(Continued)

OTHER PUBLICATIONS

Halliburton Energy Services, Inc., International Search Report and Written Opinion, PCT/US2022/030082, Feb. 16, 2023, 9 pages.

*Primary Examiner* — Freddie Kirkland, III
(74) *Attorney, Agent, or Firm* — Kilpatrick Townsend & Stockton LLP

(57) ABSTRACT

A modular gas detection system includes a primary gas chromatograph, a constant volume extractor positionable to provide a continuous fluid sample to the primary gas chromatograph, and a total hydrocarbon analyzer. The modular gas detection system also includes a processing device and a memory device including instructions executable by the processing device for causing the processing device to perform operations. The operations include adjusting a detection scheme of the primary gas chromatograph to update a detection range for the continuous fluid sample to detect different hydrocarbons within a single column. Further, the operations include controlling routing of the continuous fluid sample from the constant volume extractor to the primary gas chromatograph and the total hydrocarbon analyzer.

20 Claims, 4 Drawing Sheets

(51) Int. Cl.
    *G01N 30/68*  (2006.01)
    *G01N 30/88*  (2006.01)

(56) References Cited

U.S. PATENT DOCUMENTS

| | | |
|---|---|---|
| 9,417,220 B2 | 8/2016 | Wang et al. |
| 9,488,750 B2 * | 11/2016 | Bright ................ G01N 21/3504 |
| 11,542,449 B2 * | 1/2023 | Hinton .................... C10L 1/003 |
| 2007/0114377 A1 | 5/2007 | Qian et al. |
| 2016/0084985 A1 | 3/2016 | Bright |
| 2019/0085253 A1 | 3/2019 | Hinton et al. |

\* cited by examiner

MODULAR GAS DETECTION SYSTEM FOR A WELLBORE

TECHNICAL FIELD

The present disclosure relates generally to wellbore operations and, more particularly (although not necessarily exclusively), to systems for detecting quantities of various gas compounds extracted from a wellbore.

BACKGROUND

Detection systems may be used in a well environment to analyze fluid extracted from a wellbore. Detection systems may analyze fluid samples for various hydrocarbons as well as various inorganic compounds, such as nitrogen or carbon dioxide. Multiple separate detection systems may be used to detect a variety of organic and inorganic compounds. Presently, multiple gas detection instruments may be dedicated to a single wellbore. Current testing environments may demand separate instruments for different organic and inorganic compounds. Coordinating testing efforts and results from multiple instruments can be time consuming and leave room for error.

DETAILED DESCRIPTION

Figure 1:
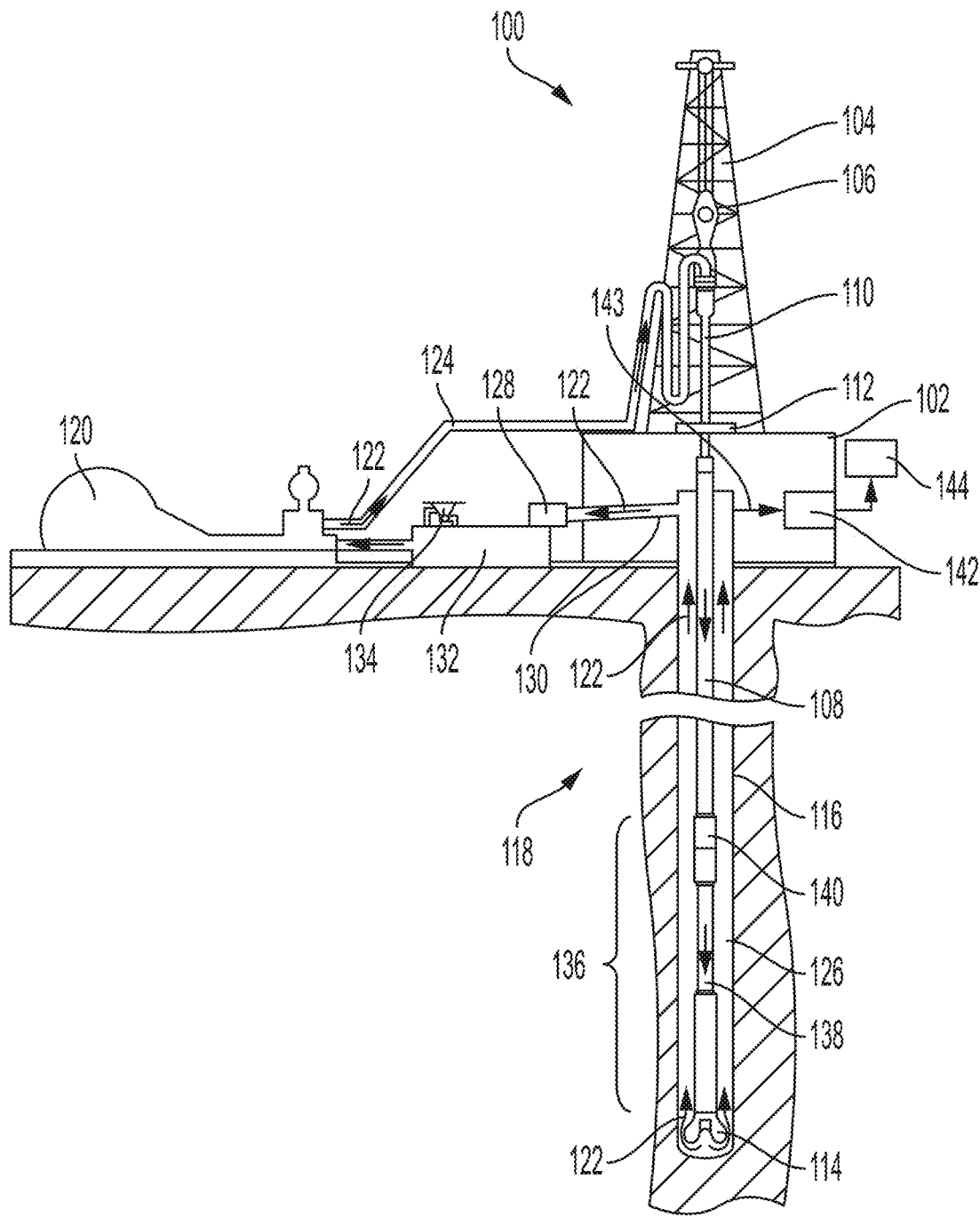
FIG. 1 is a schematic of a drilling system according to one example of the present disclosure.

Certain aspects and examples of the present disclosure relate to a modular gas detection system (MGDS) for fluid samples extracted from a wellbore. The MGDS may include a constant volume extractor, a primary gas chromatograph, a total hydrocarbon analyzer, a processing device, and a memory. The constant volume extractor may agitate a drilling mud returned to a surface to liberate entrained gases for analysis. The primary gas chromatograph may analyze a gas sample to determine an amount of a particular organic compound within the gas sample or to determine an absence of a particular organic compound within the gas sample. The total hydrocarbon analyzer may analyze a gas sample to determine a total amount of hydrocarbons within the gas sample. The MGDS may be structured to accept additional modules that detect additional compounds of the gas sample to broaden sensor readings available to the MGDS. The memory may contain instructions to cause the processor to automatically recognize and utilize additional modules as they are introduced to the MGDS by routing gas samples to the additional modules. The memory may also contain instructions to alter a drilling procedure, alter a completion procedure, or actuate a tool downhole in view of test results from any of the modules within the MGDS. The MGDS may simplify gas detection processes by unifying instruments under the control of a processing unit. The MGDS may further simplify the testing process by adjusting internal instruments, such as a gas chromatograph, to analyze a wider range of compounds detectable in a single test chamber.

The MGDS may have an instrument that is connected to a constant volume/constant temperature gas extractor or other types of extractors for real-time formational gas analysis. The instrument may have a base setup of a primary gas chromatograph and total hydrocarbon analyzer with a local or remote processing device. The primary gas chromatograph may have at least a single column with a detector that may, in some examples, be a flame ionization detector (FID). The total hydrocarbon analyzer may also be an FID. The chassis of the MGDS may also have space or connections for additional gas chromatograph instruments or single-point detectors that can be integrated into the system control. The primary gas chromatograph may be able to change detection range by engaging additional pressure or temperature controls to allow the MGDS to have dynamic pressure and temperature chromatography.

The MGDS may automatically detect an addition of a module added to the MGDS. The MGDS may automatically determine the type of module or prompt a user to input a module type. The MGDS may have the ability to run continuous quality control routines, which may be presented as a peak separation, a position, a full width at half maximum (FWHM), a shape, a signal to noise ratio, any other parameters that indicate system health and calibration stability, or any combination thereof.

The MGDS may have the ability to automatically inject a gas of known concentration to determine calibration stability and force or prompt a user to perform a calibration. Results of the recalibration process may be used to recalculate previous results from any module in the MGDS. The system may not require a person to be physically present to monitor or adjust the instrument. The MGDS may be remotely controllable or may be able to report results to a remote position. Based on the preprogrammed well program, the instrument may prompt the user to adjust methods or add or subtract modules to meet client requirements.

The gas chromatograph may be able to detect methane, ethane, ethylene, propane, propylene, i-butane, n-butane, i-pentane, n-pentane, neo-pentane, hexane, cyclohexane, methyl cyclohexane, toluene, benzene, heptane, octane and other organic compounds from within a single test chamber. In an example, the additional module for inorganic gas can detect hydrogen, helium, nitrogen, carbon dioxide, water, or other inorganic compounds.

Illustrative examples are given to introduce the reader to the general subject matter discussed herein and are not intended to limit the scope of the disclosed concepts. The following sections describe various additional features and examples with reference to the drawings in which like numerals indicate like elements, and directional descriptions are used to describe the illustrative aspects, but, like the illustrative aspects, should not be used to limit the present disclosure.

FIG. 1 is a schematic of a drilling system according to one example of the present disclosure. As illustrated, the drilling system 100 may include a drilling platform 102 that supports a derrick 104 having a traveling block 106 for raising and lowering a drill string 108. The drill string 108 may include, but is not limited to, drill pipe and coiled tubing, as generally known to those skilled in the art. A kelly 110 supports the drill string 108 as it is lowered through a rotary table 112. A drill bit 114 is attached to the distal end of the drill string 108 and is driven either by a downhole motor or by rotation of the drill string 108 from the well surface. As the bit 114 rotates, it creates a wellbore 116 that penetrates various subterranean formations 118.

While FIG. 1 generally depicts a land-based drilling assembly, those skilled in the art will readily recognize that the principles described herein are equally applicable to the subsea drilling operations that employ floating or sea-based platforms and rigs, without departing from the scope of the disclosure. The principles may also be applicable to other forms of drilling, managed pressure drilling, and underbalanced drilling.

A pump 120 (e.g., a mud pump) circulates a fluid 122 through a feed pipe 124 and into the interior of the drill string 108. In some embodiments, the fluid 122 may be a drilling fluid used in the presently described drilling system 100. However, it should be noted that the principles of the present disclosure are equally applicable to any type of fluid return or sampled fluid derived from a wellbore. Accordingly, usage of "the fluid 122" is meant to encompass, without limitation, any other type of fluid that may be circulated through a wellbore, produced at the surface at or near the platform 102, or sampled downhole and subsequently provided to the fluid extraction system 142. For instance, "the fluid 122" may equally apply to reservoir fluids, gases, oils, water, and any other fluid that may be produced from a wellbore. Moreover, the drilling system 100 may equally be replaced or otherwise equated with any wellbore fluid extraction system, such as a wellhead installation used to produce fluids to the surface.

In the drilling system 100, the fluid 122 may be conveyed via the drill string 108 to the drill bit 114 and out at least one orifice in the drill bit 114. The fluid 122 is then circulated back to the surface via an annulus 126 defined between the drill string 108 and the walls of the wellbore 116. At the surface, the recirculated or spent fluid 122 exits the annulus 126 and may be conveyed to one or more fluid processing unit(s) 128 via a fluid return line 130. After passing through the fluid processing unit(s) 128, a "cleaned" fluid 122 is deposited into a nearby retention pit 132 (i.e., a mud pit). One or more chemicals, fluids, or additives may be added to the fluid 122 via a mixing hopper 134 communicably coupled to or otherwise in the fluid communication with the retention pit 132.

The drilling system 100 may further include a bottom hole assembly (BHA) 136 arranged in the drill string 108 at or near the drill bit 114. The BHA 136 may include any of a number of sensor modules 138 (one shown) which may include formation evaluation sensors and directional sensors, such as measuring-while-drilling and/or logging-while-drilling tools. The BHA 136 may also contain fluid pulser system 140 that induces pressure fluctuations in the fluid flow. Data from the downhole sensor modules 138 may be encoded and transmitted to the surface via the pulser system 140 whose pressure fluctuations, or "pulses," propagate to the surface through the column of fluid flow in the drill string 108. At the surface the pulses are detected by one or more surface sensors (not shown), such as a pressure transducer, a flow transducer, or a combination of a pressure transducer and a flow transducer.

During the drilling operation, a discrete or continuous sample of the fluid 122 returning to the surface (i.e., the fluid returns) may be obtained and conveyed to a fluid extraction system 142 arranged at or near the drilling platform 102. The fluid extraction system 142 may include a constant volume extractor. The sample may be conveyed to the fluid extraction system 142 via a suction tube 143 fluidly coupled to a source of the fluid 122 returning to the surface. In some embodiments, for instance, the suction tube 143 may be fluidly coupled to the fluid return line 130. In other embodiments, however, the suction tube 142 may be directly coupled to the annulus 126 such that a sample of the fluid 122 may be obtained directly from the well at or near the surface of the well. For example, the fluid extraction system 142 may alternatively be arranged within the fluid return line 130 prior to the fluid processing unit(s) 128. In such an embodiment, the suction tube 143 may be omitted. In yet other embodiments, the suction tube 143 may be coupled to a possum belly at the mud tanks or a header box associated with the fluid processing unit(s) 128, without departing from the scope of the disclosure.

As described in greater detail below, the fluid extraction system 142 may include a fluid separator that extracts gases from the sample fluid 122 and analyzes the chemical composition of the extracted gases. The fluid separator may use the flow energy of the incoming sample fluid to generate increased fluid velocities that help enhance the separation process. In operation, the fluid separator may extract gases from the sample fluid based on a density or viscosity differential between the various fluidic components of the sample fluid. Once the gas is extracted from the sample fluid, the chemical composition of the fluid may then be determined with an associated analytical device or gas logging unit arranged at or near the drilling platform 102. An example gas logging unit may be a Modular Gas Detection System (MGDS). In some embodiments, the separated fluids may be stored in a container and taken off site and subsequently analyzed under laboratory conditions, without departing form the scope of the disclosure.

Once the chemical composition of the fluid is determined, the data may be transmitted (either wired or wirelessly) to one or more peripheral devices 144, either on or off site, to any interested party for consideration, for example, at a control hub remote from the location of the well from which the fluid was gathered. As will be appreciated, knowledge of the chemical composition of gases extracted from the fluid 122 can be used by an analyst, mud logger, geochemist, geologist, petro-physicist, or other well operators having knowledge of formational fluid analysis in identifying hydrocarbon-bearing zones. In addition, in applications where the fluid 122 is drilling fluid, the peripheral device 144 could be used to change the drilling parameters or drilling fluid composition. As will be appreciated, such knowledge of the chemical composition of gases extracted from the fluid 122 can equally be beneficial for well operators in drilling of other types of wells such as, but not limited to, helium, nitrogen, or geothermal wells.

The peripheral devices 144 may include, but are not limited to, a controller, a monitor (e.g., displays GUIs, etc.), a printer, an alarm, additional storage memory, etc. In some embodiments, the monitor or the printer may provide the well operator with a graphical output corresponding to a particular parameter of the extracted gas. In other embodiments, the alarm (either audible or visual) may alert the well operator that a particular gas, a concentration of a gas, or a ratio of gases, has been detected, such as high levels of $CO_2$ or $H_2S$. If the levels or ratios of such gases exceed a predetermined limit, the well operator may desire to cease the particular wellbore operation (e.g., drilling, completing, fracking, circulating, etc.) or otherwise alter one or more operational parameters.

Figure 2:
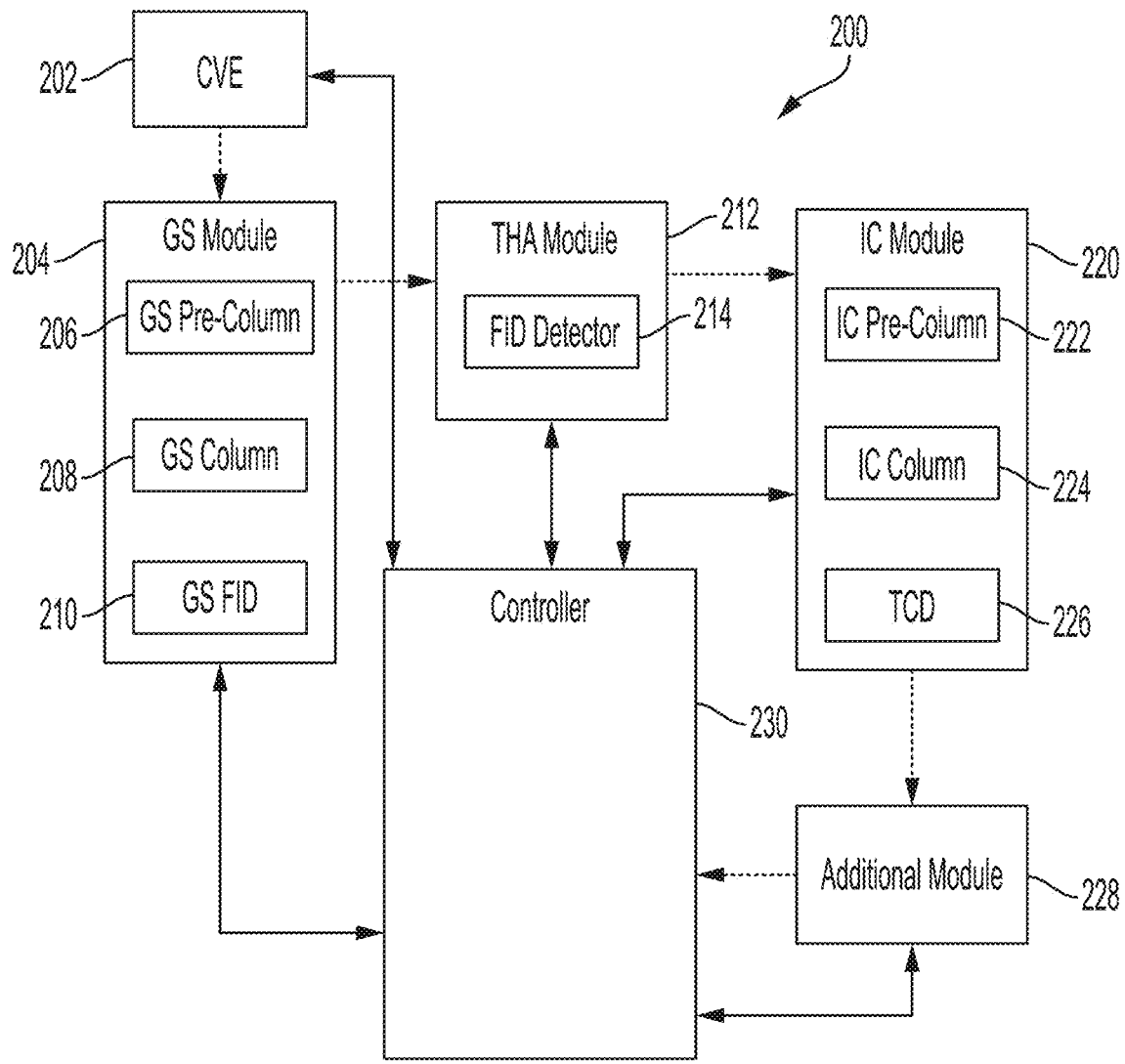
FIG. 2 is a block diagram of a modular gas detection system (MGDS) according to one example of the present disclosure.

FIG. 2 is a block diagram of a modular gas detection system (MGDS) 200 according to one example of the present disclosure. Other configurations of the MGDS 200 are also possible. The MGDS 200 may include a constant volume extractor (CVE) 202 that may provide gas samples to the testing modules within the MGDS 200. The MGDS 200 may also contain a primary gas chromatograph (GC) module 204, a total hydrocarbon analysis (THA) module 212, an inorganic compound (IC) module 220, an additional module 228, and a controller 230.

A gas sample may move from the CVE 202 to the primary GC module 204. The gas sample may enter a GC pre-column 206, where the gas sample may be combined with a hydrogen carrier gas to enhance separation efficiently and reduce test times. In some examples, an alternative carrier gas may be chosen to allow for different modules to be used, such as a mass spectrometer.

The gas sample may then move from the GC pre-column 206 to a single GC column 208 of the GC Module 204. The GC column 208 may receive pressure and temperature control signals from the controller 230. In some examples, the pressure and temperature control signals may be transmitted via open platform communications (OPC) standards over an Ethernet connection. The pressure and temperature control signals may result from adjustments to a detection scheme intended to update a detection range for a continuous fluid sample to detect different hydrocarbons within the single GC column 208.

After being adjusted for pressure and temperature, the gas sample may move to a flame ionization detector (FID) 210 of the primary gas chromatograph 204. The FID 210 may be able to detect at least methane, ethane, ethylene, propane, propylene, i-butane, n-butane, i-pentane, n-pentane, neopentane, hexane, cyclohexane, methyl cyclohexane, toluene, benzene, heptane, and octane from the contents of the single GC column 208. The GS FID 210 may adjust which compound it detects by altering cycle times. The amount of a particular hydrocarbon within the gas sample may be derived from the amount of $CO_2$ that results from a combustion controlled by the FID 210. The GS FID 210 may report test results back to the controller 230.

The GC module 204 may then move the gas sample to the THA Module 212. In some examples, the THA module 212 may obtain a gas sample directly from the CVE 202. The THA Module 212 may also use an FID 214 in analyzing the gas sample. The FID 214 may report a total amount of hydrocarbons within the gas sample, as opposed to the content of any one given compound. In an example, the FID 214 reports at least hexane, benzene, toulene, xylenes, naphthalene, and fluorene. Other hydrocarbons may also be counted towards the total hydrocarbon content detected by the FID 214 of the THA Module 212. The amount of total hydrocarbons within the gas sample may be derived from the amount of $CO_2$ that results from a combustion controlled by the FID 214. The FID 214 of the THA 212 may then report test results back to the controller 230.

The THA module 212 may then move the gas sample to the IC module 220. The IC module 220 may also have an IC Pre-Column 222 for the introduction of a carrier gas, such as hydrogen. The gas sample may then be moved to the IC column 224 where the controller 230 can adjust temperature and pressure within the IC column 224 to prepare the gas sample for the thermal conductivity detector (TCD) 226 within the IC module 220. In some examples, the IC module 220 may obtain a gas sample directly from the CVE 202 for preparation in the IC Pre-Column 222. The TCD 226 may be able to detect at least hydrogen, helium, nitrogen, sulfur oxide, and carbon dioxide with an instrument of the modular gas detection system. Other inorganic compounds may also be detected by the TCD 226. The TCD 266 may then report test results back to the controller 230.

The IC module 220 may then move the gas sample to an additional module 228. The controller 230 may be able to detect when the additional module 228 is added to the MGDS 200. Example additional modules may include additional gas chromatographs, additional thermal conductivity detectors, column banks, mass spectrometers, flame photometric detectors, electron capture detectors, or other possible modules. In an example, the additional module 228 may obtain the gas sample directly from the CVE 202. The controller 230 may prompt an entity, such as a well operator, to add a module to the gas detection system based on a detection of an unidentified compound in any module within the MGDS 200. The controller 230 may also prompt an entity to remove a module from the modular gas detection system based on the performance or health of the module. After executing at least one test, the additional module 228 may report test results back to the controller 230.

The controller 230, in some examples, may be able to initiate a built-in seft-test for the MGDS 200 that can test any module for functionality. A user may be able to define criteria for an alert issued by the built-in self-test. For example, the user may be able to define acceptable parameters for inlet pressures, outlet pressures, TCD Wheatstone bridge currents, detector temperatures, column temperatures, or sample size. The controller 230 may transmit control signals to release a gas of a known quantity and composition to calibrate any of the modules within the MGDS 200. The controller 230 may be able to identify an origin depth of a gas sample extracted by the CVE 202 based on compounds detected within the sample by the modules and a relationship between a pump volume and a wellbore volume.

Figure 3:
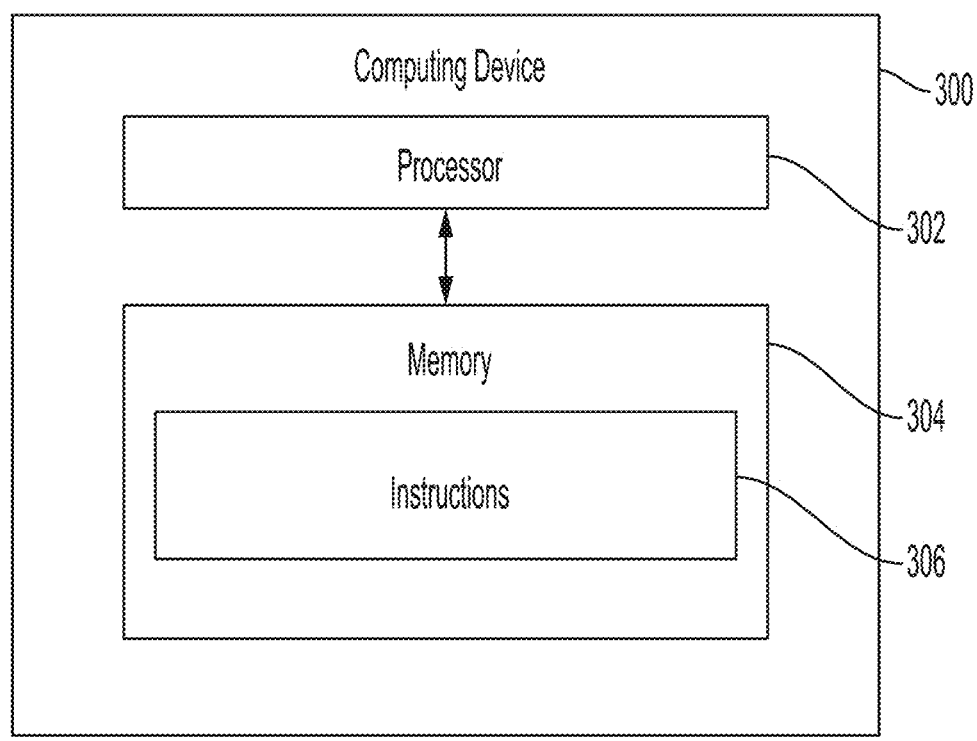
FIG. 3 is a block diagram of an example of a computing device containing instructions for implementing some aspects of the present disclosure.

FIG. 3 is a block diagram of an example of a computing device 300 containing instructions for implementing some aspects of the present disclosure. An example of the computing device 300 may be the controller 230 of FIG. 2. The system includes a processor 302 that may be communicatively coupled to a memory 304. In some examples, the processor 302 and the memory 304 can be part of the same computing device. In other examples, the processor 302 and the memory 304 can be distributed from (e.g., remote to) one another.

The processor 302 can include one processor or multiple processors. Non-limiting examples of the processor 304 include a Field-Programmable Gate Array (FPGA), an application-specific integrated circuit (ASIC), a microprocessor, etc. The processor 302 can execute instructions 306 stored in the memory 304 to perform operations. In some examples, the instructions 306 can include processor-specific instructions generated by a compiler or an interpreter from code written in a suitable computer-programming language, such as C, C++, C#, etc.

The memory 304 can include one memory or multiple memories. The memory 304 can be non-volatile and may include any type of memory that retains stored information when powered off. Non-limiting examples of the memory 304 include electrically erasable and programmable read-only memory (EEPROM), flash memory, or any other type of non-volatile memory. At least some of the memory 304 can include a non-transitory computer-readable medium from which the processor 302 can read instructions 306. A computer-readable medium can include electronic, optical, magnetic, or other storage devices capable of providing the processor 304 with computer-readable instructions or other program code. Non-limiting examples of a computer-readable medium include magnetic disk(s), memory chip(s), ROM, random-access memory (RAM), an ASIC, a configured processor, optical storage, or any other medium from which a computer processor can read the instructions 306. In some examples, the processor 302 can execute the instructions 306 to perform some or all of the functionality described herein.

Figure 4:
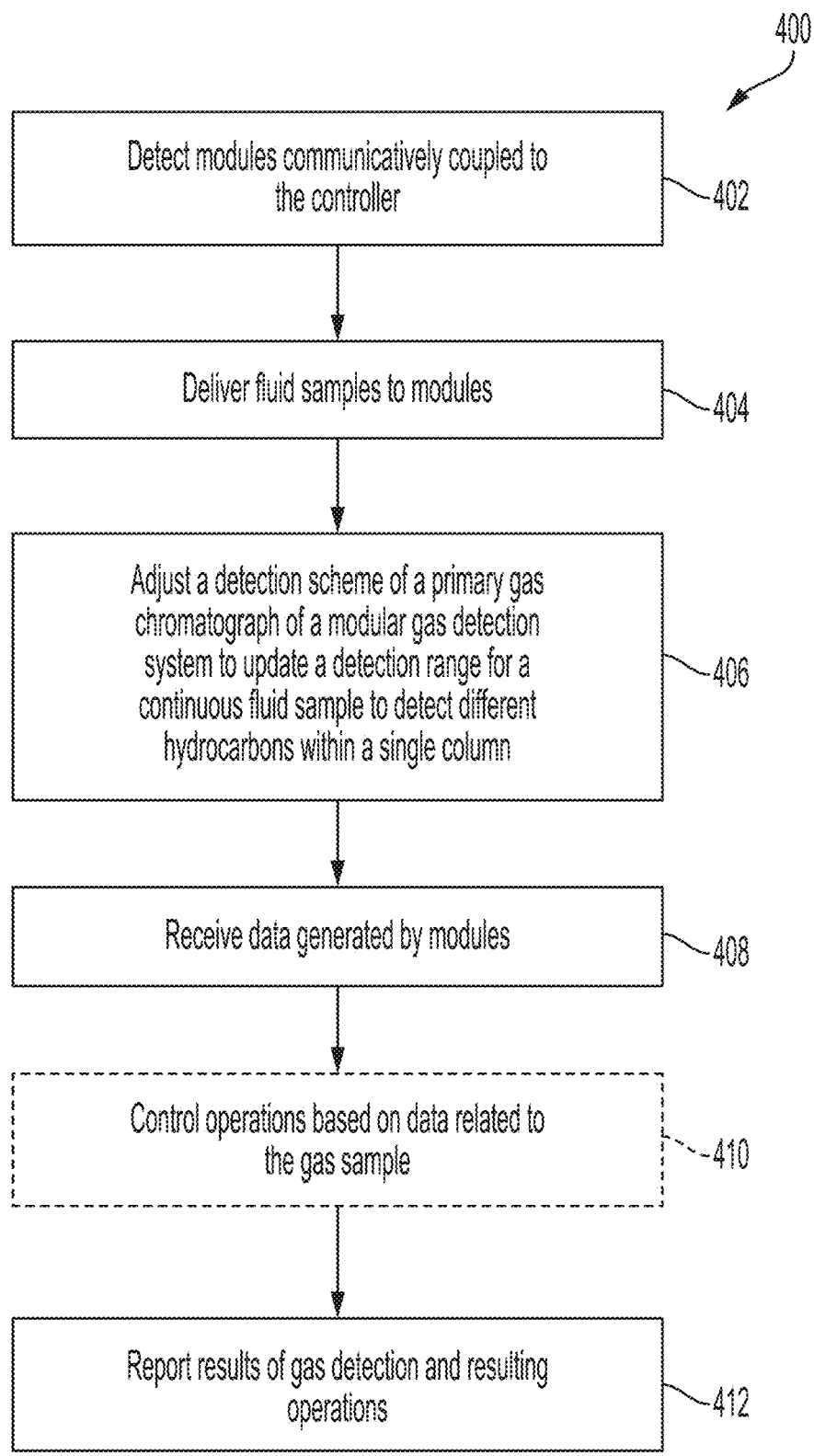
FIG. 4 is a flowchart for a process of adjusting a detection scheme of a gas chromatograph according to one example of the present disclosure.

FIG. 4 is a flowchart for a process 400 of adjusting a detection scheme of a gas chromatograph according to one example of the present disclosure. The process shown in FIG. 4 can be controlled with the computing device 300 of FIG. 3 or with other examples of a gas chromatograph according to various aspects of the present disclosure.

At block 402, the computing device 300 may detect modules communicatively coupled to the computing device 300. The computing device 300 may at least detect the primary gas chromatograph module 240 and the constant volume extractor 202. The computing device 300 may also detect the total hydrocarbon analysis module 212, the inorganic compound module 220, and additional modules. Possible additional modules may include additional gas chromatographs, additional thermal conductivity detectors, column banks, mass spectrometers, flame photometric detectors, electron capture detectors, or other possible modules. The computing device 300 may prompt an entity to add a module based on detection of an unidentified compound or prompt an entity to remove a module based on the performance health of the module.

At block 404 the computing device 300 may deliver a gas sample to a module of the modular gas detection system (MGDS) 200. In some examples, the gas sample may pass through some or all modules sequentially. In some examples, the gas sample may enter a module directly from the constant volume extractor 202. In some examples, the gas sample may be mixed with a carrier gas to enhance separation efficiency and reduce test time. Example carrier gases can include Helium, Nitrogen, Hydrogen, and Argon.

At block 406 the computing device 300 may adjust the detection scheme of the primary gas chromatograph module 204 of the Modular Gas Detection System (MGDS) 200. The processor may adjust the detection scheme by updating the detection range for the continuous fluid sample. The detection range may be adjusted to detect different hydrocarbons within a single column of the primary gas chromatograph.

The primary gas chromatograph module 204 may control the chamber with a fast temperature programmer (FTP). The FTP may resistively heat the column by applying a low-voltage current to the column coating. The FTP may resistively heat other valve zones in addition to the chromatographic column of the primary gas chromatograph module 204. As an alternative to a traditional gas chromatograph column oven, the FTP may reduce the size and mass of a heating zone within the MGDS 200. The FTP may also have faster thermal ramping and cooling cycles than a traditional column oven.

The constant volume extractor 202 may extract gas in a continuous circulation while the primary gas chromatograph 204 monitors the continuous sample to record a response over time. With the test results reported to the computing device 300 over time, an area over time may be calculated. The area over time may be used to determine the total concentration of a given compound within the gas sample. The instantaneous response of a compound detected in test may then be delated to the total response of the compound detected over time.

At block 408, the computing device 300 may receive data generated by any of the modules within the MGDS 200 related to the gas sample. The data may be transmitted via open platform communications (OPC) standards over an Ethernet connection. The data may be displayed on a monitor for a user. The data may be transmitted, interpreted, or stored remotely from the MGDS 200. The data may be processed by the computing device 300 to derive an origin depth of the gas sample. The origin depth may be derived from a relationship between a pump volume and a wellbore volume as well as the compounds detected within the gas sample.

In some examples, at block 410, the computing device 300 may alter drilling or completion operations based on data related to the gas sample. For example, the primary gas chromatograph 204 may detect a high concentration of heptane within the gas sample. The computing device 300 may compare this concentration to previous results and instruct a drilling assembly to continue drilling. In additional example, the primary gas chromatograph 204 may detect a high concentration of another compound in the gas sample that triggers a control operation by the computing device 300 to stop drilling or to change a drilling plan.

At block 412, the computing device 300 may report the results related of the gas sample and may also report any actions taken in block 410. The results may be reported to a user, a database, or any suitable computing device. In some examples, the results may be used to adjust and calibrate any module of the MGDS 200 for future tests.

In some aspects, apparatus, method, and instructions for the modular gas detection system are provided according to one or more of the following examples:

As used below, any reference to a series of examples is to be understood as a reference to each of those examples disjunctively (e.g., "Examples 1-4" is to be understood as "Examples 1, 2, 3, or 4").

Example 1 is a modular gas detection system comprising: a primary gas chromatograph; a constant volume extractor positionable to provide a continuous fluid sample to the primary gas chromatograph; a total hydrocarbon analyzer; a processing device; and a memory device including instructions executable by the processing device for causing the processing device to: adjust a detection scheme of the primary gas chromatograph to update a detection range for the continuous fluid sample to detect different hydrocarbons within a single column; and control routing of the continuous fluid sample from the constant volume extractor to the primary gas chromatograph and the total hydrocarbon analyzer.

Example 2 is the system of example 1, wherein the instructions are further executable by the processing device for causing the processing device to: detect additional modules coupled to the modular gas detection system; and controlling routing of the continuous fluid sample to the additional modules.

Example 3 is the system of examples 1-2, wherein the instructions are further executable by the processing device for causing the processing device to: prompt an entity to add a module to the modular gas detection system based on detection of an unidentified compound; and prompt the entity to remove a module from the modular gas detection system based on performance health of a module.

Example 4 is the system of examples 1-3, wherein the instructions are further executable by the processing device for causing the processing device to: identify an origin depth of a sample extracted by the constant volume extractor based on compounds detected within the sample and a relationship between a pump volume and a wellbore volume.

Example 5 is the system of examples 1-4, wherein adjusting the detection scheme of the primary gas chromatograph comprises adjusting temperature and pressure controls to detect at least methane, ethane, ethylene, propane, propylene, i-butane, n-butane, i-pentane, n-pentane, neo-pentane, hexane, cyclohexane, methyl cyclohexane, toluene, benzene, heptane, and octane.

Example 6 is the system of examples 1-5, further comprising: an inorganic gas detection instrument positionable to detect at least hydrogen, helium, nitrogen, and carbon dioxide.

Example 7 is the system of examples 1-6, wherein the instructions are further executable by the processing device for causing the processing device to: actuate a chamber to inject a gas of a known concentration to the primary gas chromatograph and the total hydrocarbon analyzer to calibrate the primary gas chromatograph and the total hydrocarbon analyzer.

Example 8 is the system of examples 1-7, wherein the instructions are further executable by the processing device for causing the processing device to execute a built-in self-test on modules within the system.

Example 9 is a method comprising: detecting, by a controller of a modular gas detection system, modules communicatively coupled to the controller; controlling, by the controller of the modular gas detection system, routing of a gas sample to the modules of the modular gas detection system; adjusting, by the controller of the modular gas detection system, a detection scheme of a primary gas chromatograph of the modular gas detection system to update a detection range for a continuous fluid sample to detect different hydrocarbons within a single column; receiving, by the controller of the modular gas detection system, data generated by the modules of the modular gas detection system; and reporting results, by the controller of the modular gas detection system, to an entity.

Example 10 is the method of example 9, further comprising: executing, by the controller of the modular gas detection system, drilling operations based on the data generated by the modules.

Example 11 is the method of examples 9-10, further comprising: prompting, by the controller of the modular gas detection system, the entity to add a module to the modular gas detection system based on detection of an unidentified compound; and prompting, by the controller of the modular gas detection system, the entity to remove a module from the modular gas detection system based on a performance health of the module.

Example 12 is the method of examples 9-11, further comprising: identifying, by the controller of the modular gas detection system, an origin depth of a sample extracted by a constant volume extractor based on compounds detected within the sample by the primary gas chromatograph or a total hydrocarbon analyzer of the modular gas detection system and a relationship between a pump volume and a wellbore volume.

Example 13 is the method of examples 9-12, further comprising: adjusting, by the controller of the modular gas detection system, temperature and pressure controls of the primary gas chromatograph to detect at least methane, ethane, ethylene, propane, propylene, i-butane, n-butane, i-pentane, n-pentane, neo-pentane, hexane, cyclohexane, methyl cyclohexane, toluene, benzene, heptane, and octane.

Example 14 is the method of examples 9-13, further comprising: detecting, by the controller of the modular gas detection system, inorganic compounds of at least hydrogen, helium, nitrogen, and carbon dioxide with an instrument of the modular gas detection system.

Example 15 is the method of examples 9-14, further comprising: executing, by the controller of the modular gas detection system, a built-in self-test on modules within the modular gas detection system.

Example 16 is a non-transitory computer-readable medium comprising instructions that are executable by a processing device for causing the processing device to: detect modules communicatively coupled to a controller of a modular gas detection system; control routing of a gas sample to the modules of the modular gas detection system; adjust a detection scheme of a primary gas chromatograph of the modular gas detection system to update a detection range for a continuous fluid sample to detect different hydrocarbons within a single column; receive data generated by the modules of the modular gas detection system; and control drilling or completion operations based on the data generated by the modules.

Example 17 is the non-transitory computer-readable medium of example 16, further comprising instructions that are executable by the processing device for causing the processing device to: execute drilling operations based on the data generated by the modules.

Example 18 is the non-transitory computer-readable medium of examples 16-17, further comprising instructions that are executable by a processing device for causing the processing device to: prompt an entity to add a module to the modular gas detection system based on detection of an unidentified compound; and prompt the entity to remove a module from the modular gas detection system based on a performance health of the module.

Example 19 is the non-transitory computer-readable medium of examples 16-18, further comprising instructions that are executable by a processing device for causing the processing device to: identify an origin depth of a sample extracted by a constant volume extractor based on compounds detected within the sample by the primary gas chromatograph or a total hydrocarbon analyzer of the modular gas detection system and a relationship between a pump volume and a wellbore volume.

Example 20 is the non-transitory computer-readable medium of examples 16-20, further comprising instructions that are executable by a processing device for causing the processing device to: adjust temperature and pressure controls of the primary gas chromatograph to detect at least methane, ethane, ethylene, propane, propylene, i-butane, n-butane, i-pentane, n-pentane, neo-pentane, hexane, cyclohexane, methyl cyclohexane, toluene, benzene, heptane, and octane.

The foregoing description of certain examples, including illustrated examples, has been presented only for the purpose of illustration and description and is not intended to be exhaustive or to limit the disclosure to the precise forms disclosed. Numerous modifications, adaptations, and uses thereof will be apparent to those skilled in the art without departing from the scope of the disclosure.

What is claimed is:
1. A modular gas detection system comprising:
   a primary gas chromatograph;
   a constant volume extractor positionable to provide a continuous fluid sample to the primary gas chromatograph;
   a total hydrocarbon analyzer;
   a processing device; and
   a memory device including instructions executable by the processing device for causing the processing device to:

adjust a detection scheme of the primary gas chromatograph to update a detection range for the continuous fluid sample to detect different hydrocarbons within a single column; and control routing of the continuous fluid sample from the constant volume extractor to the primary gas chromatograph and the total hydrocarbon analyzer.

2. The system of claim 1, wherein the instructions are further executable by the processing device for causing the processing device to:

detect additional modules coupled to the modular gas detection system; and controlling routing of the continuous fluid sample to the additional modules.

3. The system of claim 1, wherein the instructions are further executable by the processing device for causing the processing device to:

prompt an entity to add a module to the modular gas detection system based on detection of an unidentified compound; and prompt the entity to remove a module from the modular gas detection system based on performance health of a module.

4. The system of claim 1, wherein the instructions are further executable by the processing device for causing the processing device to:

identify an origin depth of a sample extracted by the constant volume extractor based on compounds detected within the sample and a relationship between a pump volume and a wellbore volume.

5. The system of claim 1, wherein adjusting the detection scheme of the primary gas chromatograph comprises adjusting temperature and pressure controls to detect at least methane, ethane, ethylene, propane, propylene, i-butane, n-butane, i-pentane, n-pentane, neo-pentane, hexane, cyclohexane, methyl cyclohexane, toluene, benzene, heptane, and octane.

6. The system of claim 1, further comprising:

an inorganic gas detection instrument positionable to detect at least hydrogen, helium, nitrogen, and carbon dioxide.

7. The system of claim 1, wherein the instructions are further executable by the processing device for causing the processing device to:

actuate a chamber to inject a gas of a known concentration to the primary gas chromatograph and the total hydrocarbon analyzer to calibrate the primary gas chromatograph and the total hydrocarbon analyzer.

8. The system of claim 1, wherein the instructions are further executable by the processing device for causing the processing device to execute a built-in self-test on modules within the system.

9. A method comprising:

detecting, by a controller of a modular gas detection system, modules communicatively coupled to the controller;

controlling, by the controller of the modular gas detection system, routing of a gas sample to the modules of the modular gas detection system;

adjusting, by the controller of the modular gas detection system, a detection scheme of a primary gas chromatograph of the modular gas detection system to update a detection range for a continuous fluid sample to detect different hydrocarbons within a single column;

receiving, by the controller of the modular gas detection system, data generated by the modules of the modular gas detection system; and reporting results, by the controller of the modular gas detection system, to an entity.

10. The method of claim 9, further comprising:

executing, by the controller of the modular gas detection system, drilling operations based on the data generated by the modules.

11. The method of claim 9, further comprising:

prompting, by the controller of the modular gas detection system, the entity to add a module to the modular gas detection system based on detection of an unidentified compound; and prompting, by the controller of the modular gas detection system, the entity to remove a module from the modular gas detection system based on a performance health of the module.

12. The method of claim 9, further comprising:

identifying, by the controller of the modular gas detection system, an origin depth of a sample extracted by a constant volume extractor based on compounds detected within the sample by the primary gas chromatograph or a total hydrocarbon analyzer of the modular gas detection system and a relationship between a pump volume and a wellbore volume.

13. The method of claim 9, further comprising:

adjusting, by the controller of the modular gas detection system, temperature and pressure controls of the primary gas chromatograph to detect at least methane, ethane, ethylene, propane, propylene, i-butane, n-butane, i-pentane, n-pentane, neo-pentane, hexane, cyclohexane, methyl cyclohexane, toluene, benzene, heptane, and octane.

14. The method of claim 9, further comprising:

detecting, by the controller of the modular gas detection system, inorganic compounds of at least hydrogen, helium, nitrogen, and carbon dioxide with an instrument of the modular gas detection system.

15. The method of claim 9, further comprising:

executing, by the controller of the modular gas detection system, a built-in self-test on modules within the modular gas detection system.

16. A non-transitory computer-readable medium comprising instructions that are executable by a processing device for causing the processing device to:

detect modules communicatively coupled to a controller of a modular gas detection system;

control routing of a gas sample to the modules of the modular gas detection system;

adjust a detection scheme of a primary gas chromatograph of the modular gas detection system to update a detection range for a continuous fluid sample to detect different hydrocarbons within a single column;

receive data generated by the modules of the modular gas detection system; and control drilling or completion operations based on the data generated by the modules.

17. The non-transitory computer-readable medium of claim 16, further comprising instructions that are executable by the processing device for causing the processing device to:

execute drilling operations based on the data generated by the modules.

18. The non-transitory computer-readable medium of claim 16, further comprising instructions that are executable by a processing device for causing the processing device to:

prompt an entity to add a module to the modular gas detection system based on detection of an unidentified compound; and prompt the entity to remove a module from the modular gas detection system based on a performance health of the module.

19. The non-transitory computer-readable medium of claim 16, further comprising instructions that are executable by a processing device for causing the processing device to:

identify an origin depth of a sample extracted by a constant volume extractor based on compounds detected within the sample by the primary gas chromatograph or a total hydrocarbon analyzer of the modular gas detection system and a relationship between a pump volume and a wellbore volume.

20. The non-transitory computer-readable medium of claim 16, further comprising instructions that are executable by a processing device for causing the processing device to:

adjust temperature and pressure controls of the primary gas chromatograph to detect at least methane, ethane, ethylene, propane, propylene, i-butane, n-butane, i-pentane, n-pentane, neo-pentane, hexane, cyclohexane, methyl cyclohexane, toluene, benzene, heptane, and octane.

* * * * *